US010351635B2

(12) United States Patent
Choi et al.

(10) Patent No.: US 10,351,635 B2
(45) Date of Patent: Jul. 16, 2019

(54) METHOD FOR PREPARING RUBBER COMPOSITION USING AMINOSILANE-BASED TERMINAL MODIFIER INTRODUCING FUNCTIONAL GROUP, AND RUBBER COMPOSITION PREPARED THEREBY

(71) Applicant: LG Chem, Ltd., Seoul (KR)

(72) Inventors: Seung-Ho Choi, Daejeon (KR); Min-Soo Kim, Daejeon (KR); Cheol-Jae Kim, Daejeon (KR); Zeong-Back Kim, Daejeon (KR); Ji-Eun Kim, Daejeon (KR); Won-Mun Choi, Daejeon (KR); Dae-June Joe, Daejeon (KR)

(73) Assignee: LG Chem, Ltd. (KR)

( * ) Notice: Subject to any disclaimer, the term of this patent is extended or adjusted under 35 U.S.C. 154(b) by 34 days.

(21) Appl. No.: 15/558,453

(22) PCT Filed: Jun. 17, 2016

(86) PCT No.: PCT/KR2016/006489
§ 371 (c)(1),
(2) Date: Sep. 14, 2017

(87) PCT Pub. No.: WO2016/204575
PCT Pub. Date: Dec. 22, 2016

(65) Prior Publication Data
US 2018/0066077 A1 Mar. 8, 2018

(30) Foreign Application Priority Data
Jun. 19, 2015 (KR) .................. 10-2015-0087459

(51) Int. Cl.
| | | |
|---|---|---|
| C07C 291/00 | (2006.01) |
| C07F 7/02 | (2006.01) |
| C08L 9/00 | (2006.01) |
| C08L 9/06 | (2006.01) |
| C08F 8/30 | (2006.01) |
| C08F 36/06 | (2006.01) |
| C08F 236/06 | (2006.01) |
| C08F 236/10 | (2006.01) |
| B60C 1/00 | (2006.01) |
| C08C 19/25 | (2006.01) |
| C08K 3/00 | (2018.01) |
| C08K 3/013 | (2018.01) |
| C08K 3/04 | (2006.01) |
| C08K 3/36 | (2006.01) |
| C08C 19/22 | (2006.01) |
| C08C 19/44 | (2006.01) |
| C08L 15/00 | (2006.01) |
| C07F 7/18 | (2006.01) |
| C07F 7/08 | (2006.01) |

(52) U.S. Cl.
CPC ............ *C08C 19/25* (2013.01); *B60C 1/0016* (2013.01); *C08C 19/22* (2013.01); *C08C 19/44* (2013.01); *C08F 236/10* (2013.01); *C08K 3/00* (2013.01); *C08K 3/013* (2018.01); *C08K 3/04* (2013.01); *C08K 3/36* (2013.01); *C08L 15/00* (2013.01); *C07C 291/00* (2013.01); *C07F 7/081* (2013.01); *C07F 7/0834* (2013.01); *C07F 7/1804* (2013.01); *C08F 8/30* (2013.01); *C08F 36/06* (2013.01); *C08F 236/06* (2013.01); *C08L 9/00* (2013.01); *C08L 9/06* (2013.01)

(58) Field of Classification Search
CPC .... C08L 9/00; C08L 9/06; C08F 36/06; C08F 236/06; C08F 236/10; C07F 7/081
See application file for complete search history.

(56) References Cited

U.S. PATENT DOCUMENTS

| | | | | |
|---|---|---|---|---|
| 9,822,192 B2 * | 11/2017 | Choi | ........................ | C08F 36/06 |
| 9,951,150 B2 * | 4/2018 | Choi | ........................ | C08F 36/06 |
| 2005/0075469 A1 | 4/2005 | Feng | | |
| 2014/0243476 A1 | 8/2014 | Lee et al. | | |
| 2016/0159957 A1 | 6/2016 | Choi et al. | | |
| 2017/0002104 A1 | 1/2017 | Choi et al. | | |
| 2018/0072851 A1 * | 3/2018 | Kim | ........................ | C08C 19/44 |

FOREIGN PATENT DOCUMENTS

| | | |
|---|---|---|
| EP | 3103817 A1 | 12/2016 |
| JP | 2013-060525 A | 4/2013 |
| JP | 2013-082842 A | 5/2013 |
| JP | 2013-245248 A | 12/2013 |
| JP | 5451167 B2 | 3/2014 |
| KR | 2007-0024458 A | 3/2007 |
| KR | 2013-0090811 A | 8/2013 |
| KR | 20150032210 A | 3/2015 |
| KR | 20150056484 A | 5/2015 |
| KR | 2016-0076418 A | 6/2016 |

OTHER PUBLICATIONS

International Search Report From PCT/KR2016/006489 dated Oct. 13, 2016.
Extended European Search Report including Written Opinion for EP16811988.1 dated Jun. 8, 2018.

* cited by examiner

*Primary Examiner* — Richard A Huhn
(74) *Attorney, Agent, or Firm* — Lerner, David, Littenberg, Krumholz & Menlik, LLP

(57) ABSTRACT

The present invention relates to a terminal modified and conjugated diene-based polymer rubber composition including a terminal modified and conjugated diene-based polymer which is characterized in that an aminosilane-based terminal modifier represented by Formula 1 or Formula 2 is combined at the terminal of a conjugated diene-based polymer, and a method for preparing the same.

11 Claims, No Drawings

METHOD FOR PREPARING RUBBER COMPOSITION USING AMINOSILANE-BASED TERMINAL MODIFIER INTRODUCING FUNCTIONAL GROUP, AND RUBBER COMPOSITION PREPARED THEREBY

CROSS-REFERENCE TO RELATED APPLICATION

This application is a national phase entry under 35 U.S.C. § 371 of International Application No. PCT/KR2016/006489, filed Jun. 17, 2016, which claims priority to Korean Patent Application No. 10-2015-0087459, filed Jun. 19, 2015, the disclosures of which are incorporated herein by reference.

TECHNICAL FIELD

The present invention relates to a method for preparing a rubber composition including a terminal modified and conjugated diene-based copolymer which is prepared by using an aminosilane-based terminal modifier introducing a functional group, and a rubber composition prepared thereby.

BACKGROUND ART

With respect to the latest trends in the automobile industry, durability, stability and lowering of fuel consumption are constant requirements, and efforts to satisfy such requirements are continuously underway.

In particular, many attempts have been made at reinforcing the physical properties of rubber which is a material for automotive tires—specifically, tire treads which make direct contact with the ground. As a rubber composition for automotive tires, a rubber composition containing a conjugated diene-based polymer such as polybutadiene and a butadiene-styrene polymer is used.

Currently, studies on combining a conjugated diene-based rubber composition with various reinforcing materials are conducted in order to reinforce the performance of automotive tires. In particular, owing to increasing requirement on stability, durability and lowering of fuel consumption in an automobile, research is being conducted on a rubber composition having excellent mechanical strength including abrasion and processability as a material of automotive tires, specifically, as a material of a tire tread which makes contact with the ground.

DISCLOSURE OF THE INVENTION

Technical Problem

The object of the present invention is to provide a method for preparing a conjugated diene-based rubber composition useful as a material of a tire tread having high performance, which has low hysteresis loss without damaging abrasion resistance and breaking properties and improved wet skid properties at the same time, or low hysteresis loss without damaging wet skid properties and improved abrasion resistance and breaking properties at the same time in balance, and a terminal modified and conjugated diene-based polymer rubber composition prepared thereby.

Technical Solution

To solve the above-described tasks, the present invention provides a terminal modified and conjugated diene-based polymer rubber composition, including a terminal modified and conjugated diene-based polymer in which an aminosilane-based terminal modifier represented by the following Formula 1 or Formula 2 is combined at a terminal of a conjugated diene-based polymer:

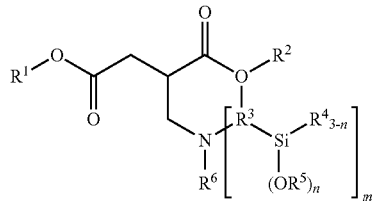

[Formula 1]

In Formula 1, $R^1$ and $R^2$ are $C_{1-20}$ hydrocarbon or $C_{1-20}$ hydrocarbon containing a heteroatom, $R^3$ is $C_{1-10}$ hydrocarbon, $R^4$ and $R^5$ are $C_{1-20}$ hydrocarbon, $R^6$ is $C_{1-10}$ hydrocarbon when m is 1, n is an integer of 1-3, and m is an integer of 1-2.

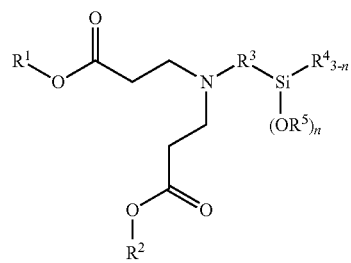

[Formula 2]

In Formula 2, $R^1$ and $R^2$ are $C_{1-20}$ hydrocarbon or $C_{1-20}$ hydrocarbon containing a heteroatom, $R^3$ is $C_{1-10}$ hydrocarbon, $R^4$ and $R^5$ are $C_{1-20}$ hydrocarbon, and n is an integer of 1-3.

According to another aspect of the present invention, there is provided a method for preparing a terminal modified and conjugated diene-based polymer rubber composition, including a) polymerizing a conjugated diene-based monomer, or a conjugated diene-based monomer and an aromatic vinyl-based monomer in a solvent in the presence of an organometallic compound to form an active polymer having an alkali metal terminal; b) injecting a compound represented by the following Formula 1 or Formula 2 to the active polymer having an alkali metal terminal and modifying to form a terminal modified and conjugated diene-based polymer; and c) preparing a terminal modified and conjugated diene-based polymer rubber composition containing the terminal modified and conjugated diene-based polymer:

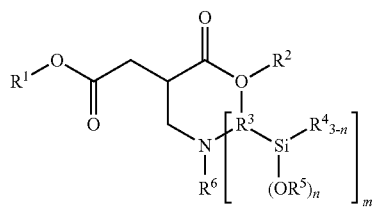

[Formula 1]

In Formula 1, $R^1$ and $R^2$ are $C_{1-20}$ hydrocarbon or $C_{1-20}$ hydrocarbon containing a heteroatom, $R^3$ is $C_{1-10}$ hydrocarbon, $R^4$ and $R^5$ are $C_{1-20}$ hydrocarbon, $R^6$ is $C_{1-10}$ hydrocarbon when m is 1, n is an integer of 1-3, and m is an integer of 1-2.

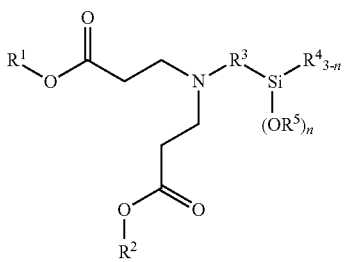

[Formula 2]

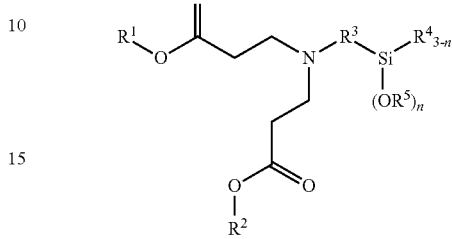

[Formula 2]

In Formula 2, $R^1$ and $R^2$ are $C_{1-20}$ hydrocarbon or $C_{1-20}$ hydrocarbon containing a heteroatom, $R^3$ is $C_{1-10}$ hydrocarbon, $R^4$ and $R^5$ are $C_{1-20}$ hydrocarbon, and n is an integer of 1-3.

According to further another aspect of the present invention, there is provided a tire or a tire tread, including the terminal modified and conjugated diene-based polymer rubber composition.

Advantageous Effects

According to the present invention, a terminal modified and conjugated diene-based polymer may be prepared using an aminosilane-based terminal modifier introducing a functional group, and a terminal modified and conjugated diene-based rubber composition useful as a material of a tire tread having high performance, which has excellent processability when being combined with silica and has low hysteresis loss without damaging abrasion resistance and breaking properties and improved wet skid properties at the same time, or low hysteresis loss without damaging wet skid properties and improved abrasion resistance and breaking properties at the same time in balance, may be prepared.

BEST MODE FOR CARRYING OUT THE INVENTION

Hereinafter, the present invention will be described in more detail.

The terminal modified and conjugated diene-based polymer rubber composition according to an aspect of the present invention includes a terminal modified and conjugated diene-based polymer in which an aminosilane-based terminal modifier represented by the following Formula 1 or Formula 2 is combined at a terminal of a conjugated diene-based polymer:

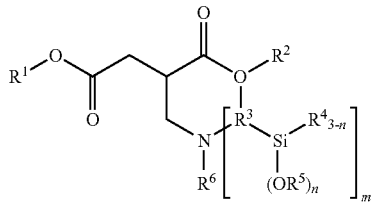

[Formula 1]

In Formula 1, $R^1$ and $R^2$ are $C_{1-20}$ hydrocarbon or $C_{1-20}$ hydrocarbon containing a heteroatom, $R^3$ is $C_{1-10}$ hydrocarbon, $R^4$ and $R^5$ are $C_{1-20}$ hydrocarbon, $R^6$ is $C_{1-10}$ hydrocarbon when m is 1, n is an integer of 1-3, and m is an integer of 1-2.

In Formula 2, $R^1$ and $R^2$ are $C_{1-20}$ hydrocarbon or $C_{1-20}$ hydrocarbon containing a heteroatom, $R^3$ is $C_{1-10}$ hydrocarbon, $R^4$ and $R^5$ are $C_{1-20}$ hydrocarbon, and n is an integer of 1-3.

In Formula 1, the heteroatom may preferably be N, S or O.

In Formula 1, $R^1$ and $R^2$ may be $C_{1-10}$ alkyl, or $C_{1-10}$ alkyl containing a heteroatom.

In Formula 1, $R^3$ may be $C_{1-10}$ alkylene.

In Formula 1, $R^4$ and $R^5$ may be $C_{1-20}$ alkyl.

In Formula 1, $R^6$ may be $C_{1-10}$ alkyl when m is 1. In the case where m is 2, the compound of Formula 1 is not substituted with $R^6$.

In Formula 2, the heteroatom may preferably be N, S or O.

In Formula 2, $R^1$ and $R^2$ may be $C_{1-10}$ alkyl, or $C_{1-10}$ alkyl containing a heteroatom.

In Formula 2, $R^3$ may be $C_{1-10}$ alkylene.

In Formula 2, $R^4$ and $R^5$ may be $C_{1-20}$ alkyl.

The terminal modified and conjugated diene-based polymer rubber composition may include 100 parts by weight of the terminal modified and conjugated diene-based polymer, and 0.1 to 200 parts by weight of an inorganic filler.

The inorganic filler may be included in an amount of, for example, 10 to 150 parts by weight, or 50 to 100 parts by weight.

The inorganic filler may be at least one selected from the group consisting of a silica-based filler, carbon black, and a mixture thereof. In the case where the filer is a silica-based filler, dispersibility may be significantly improved, and hysteresis loss may be greatly decreased due to the combination of silica particles with the terminal of the modified and conjugated diene-based polymer of the present invention.

The terminal modified and conjugated diene-based polymer rubber composition may further include a different second conjugated diene-based polymer.

The second conjugated diene-based polymer may be styrene-butadiene rubber (SBR), isoprene rubber, or a mixture thereof. The SBR may be, for example, solution styrene-butadiene rubber (SSBR).

If the second conjugated diene-based polymer is further included, the terminal modified and conjugated diene-based polymer rubber composition may include, for example, 20 to 100 parts by weight of the terminal modified and conjugated diene-based polymer and 0 to 80 parts by weight of the second conjugated diene-based polymer.

In another embodiment, the terminal modified and conjugated diene-based polymer rubber composition may include 20 to 99 parts by weight of the terminal modified and conjugated diene-based polymer and 1 to 80 parts by weight of the second conjugated diene-based polymer.

In another embodiment, the terminal modified and conjugated diene-based polymer rubber composition may include 10 to 100 parts by weight of the terminal modified and conjugated diene-based polymer, 0 to 90 parts by weight of the second conjugated diene-based polymer, 0 to 100 parts by weight of carbon black, 5 to 200 parts by weight of silica, and 2 to 20 parts by weight of a silane coupling agent.

In another embodiment, the terminal modified and conjugated diene-based polymer rubber composition may include to 100 parts by weight of the terminal modified and conjugated diene-based polymer, 0 to 90 parts by weight of the second conjugated diene-based polymer, 0 to 100 parts by weight of carbon black, 5 to 200 parts by weight of silica, and 2 to 20 parts by weight of a silane coupling agent, wherein the sum of the terminal modified and conjugated diene-based polymer and the second conjugated diene-based polymer may be 100 parts by weight.

In another embodiment, the terminal modified and conjugated diene-based polymer rubber composition may include 10 to 99 wt % of the terminal modified and conjugated diene-based polymer, 1 to 90 wt % of the second conjugated diene-based polymer, 1 to 100 parts by weight of carbon black, 5 to 200 parts by weight of silica, and 2 to 20 parts by weight of a silane coupling agent.

In addition, the terminal modified and conjugated diene-based polymer rubber composition may further include 1 to 100 parts by weight of an oil. The oil may be, for example, a mineral oil or a softening agent.

The oil may be used in an amount of 10 to 100 parts by weight or 20 to 80 parts by weight based on 100 parts by weight of a conjugated diene-based polymer. In this range, physical properties may be exhibited well, and a rubber composition may be appropriately softened so as to have good processability.

The method for preparing a terminal modified and conjugated diene-based polymer rubber composition according to another aspect of the present invention includes polymerizing a conjugated diene-based monomer, or a conjugated diene-based monomer and an aromatic vinyl-based monomer in a solvent in the presence of an organometallic compound to form an active polymer having an alkali metal terminal; b) injecting a compound represented by the following Formula 1 or Formula 2 to the active polymer having an alkali metal terminal and modifying to form a terminal modified and conjugated diene-based polymer; and c) preparing a terminal modified and conjugated diene-based polymer rubber composition containing the terminal modified and conjugated diene-based polymer:

[Formula 1]

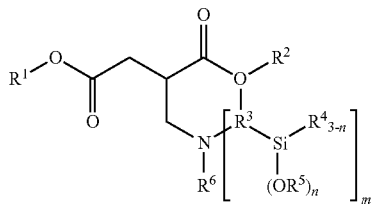

In Formula 1, $R^1$ and $R^2$ are $C_{1-20}$ hydrocarbon or $C_{1-20}$ hydrocarbon containing a heteroatom, $R^3$ is $C_{1-10}$ hydrocarbon, $R^4$ and $R^5$ are $C_{1-20}$ hydrocarbon, $R^6$ is $C_{1-10}$ hydrocarbon when m is 1, n is an integer of 1-3, and m is an integer of 1-2.

[Formula 2]

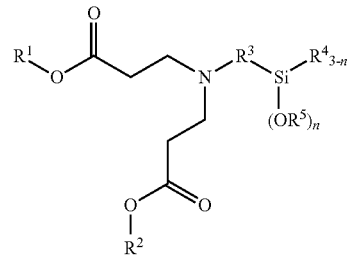

In Formula 2, $R^1$ and $R^2$ are $C_{1-20}$ hydrocarbon or $C_{1-20}$ hydrocarbon containing a heteroatom, $R^3$ is $C_{1-10}$ hydrocarbon, $R^4$ and $R^5$ are $C_{1-20}$ hydrocarbon, and n is an integer of 1-3.

The conjugated diene-based monomer may be, for example, at least one selected from the group consisting of 1,3-butadiene, 2,3-dimethyl-1,3-butadiene, piperylene, 3-butyl-1,3-octadiene, isoprene, and 2-phenyl-1,3-butadiene.

The aromatic vinyl-based monomer may be, for example, at least one selected from the group consisting of styrene, α-methylstyrene, 3-methylstyrene, 4-methylstyrene, 4-propylstyrene, 1-vinylnaphthalene, 4-cyclohexylstyrene, 4-(p-methylphenyl)styrene, and 1-vinyl-5-hexvinaphthalene, and in another embodiment, styrene or α-methylstyrene may be used.

The solvent is not specifically limited and may be any solvent applicable to the homopolymerization or copolymerization of the conjugated diene-based monomer, for example, hydrocarbon or at least one selected from the group consisting of n-pentane, n-hexane, n-heptane, isooctane, cyclohexane, toluene, benzene and xylene.

The organometallic compound may be an organoalkali metal compound, or may be at least one selected from the group consisting of an organolithium compound, an organosodium compound, an organopotassium compound, an organorubidium compound, and an organocesium compound.

In an embodiment, the organometallic compound may be at least one selected from the group consisting of methyllithium, ethyllithium, isopropyllithium, n-butyllithium, sec-butyllithium, tert-butyllithium, n-decyllithium, tert-octyllithium, phenyllithium, 1-naphthyllithium, n-eicosyllithium 4-butylphenyllithium, 4-tolyllithium, cyclohexyllithium, 3,5-di-n-heptylcyclohexyllithium and 4-cyclopentyllithium. Preferably, the organometallic compound may be n-butyllithium, sec-butyllithium, or a mixture thereof.

In another embodiment, the organometallic compound may be at least one selected from the group consisting of sodium naphthalide, potassium naphthalide, lithium alkoxide, sodium alkoxide, potassium alkoxide, lithium sulfonate, sodium sulfonate, potassium sulfonate, lithium amide, sodium amide and potassium amide, and may be used together with another organometallic compound.

In an embodiment of the present invention, the organometallic compound may be used in a molar amount of 0.01 to 10 mmol, 0.05 to 5 mmol, 0.1 to 2 mmol, or 0.1 to 1 mmol based on 100 g of the total amount of the monomer. If the molar amount of the organometallic compound satisfies this range, an optimized conjugated diene-based polymer for preparing a terminal modified and conjugated diene-based polymer may be obtained.

The molar ratio of the organometallic compound and the compound represented by Formula 1 or Formula 2 is, for example, 1:0.1 to 1:10, preferably, 1:0.3 to 1:2. In the case where the molar ratio satisfies this range, a conjugated diene-based polymer may be imparted with a modification reaction with optimized performance.

The active polymer having a metal terminal means a polymer in which a polymer anion and a metal cation are combined.

In Formula 1, the heteroatom is preferably N, S or O.

In Formula 1, $R^1$ and $R^2$ may be $C_{1-10}$ alkyl, or $C_{1-10}$ alkyl containing a heteroatom.

In Formula 1, $R^3$ may be $C_{1-10}$ alkylene.

In Formula 1, $R^4$ and $R^5$ may be $C_{1-20}$ alkyl.

In Formula 1, $R^6$ may be $C_{1-10}$ alkyl when m is 1. In the case where m is 2, the compound of Formula 1 is not substituted with $R^6$.

In Formula 2, the heteroatom may preferably be N, S or O.

In Formula 2, $R^1$ and $R^2$ may be $C_{1-10}$ alkyl, or $C_{1-10}$ alkyl containing a heteroatom.

In Formula 2, $R^3$ may be $C_{1-10}$ alkylene.

In Formula 2, $R^4$ and $R^5$ may be $C_{1-20}$ alkyl.

The compound represented by Formula 1 or Formula 2 is an aminosilane-based terminal modifier, and is an aminosilane derivative substituted with a group including a tertiary amine group, a group having silica affinity such as an ethylene glycol group, or a nucleophilic group such as alkyl or aryl at the same time. The tertiary amine group in the terminal modifier improves the dispersibility of silica and plays the role of a catalyst during the reaction, and the group having silica affinity reacts with silica to play the role of improving the abrasion properties and processability of a polymer. In addition, a modifier including a nucleophilic group may increase the solubility of a polymer in hexane and increase the modifying ratio of a polymer.

Preferably, the compound represented by Formula 1 may be represented by the following Formula 1a:

[Formula 1a]

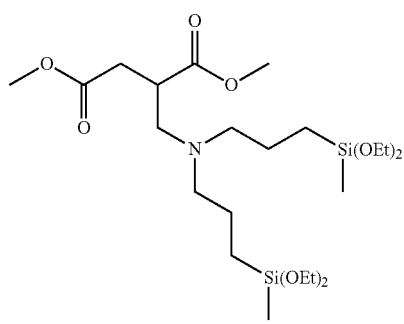

Preferably, the compound represented by Formula 2 may be represented by the following Formula 2a:

[Formula 2a]

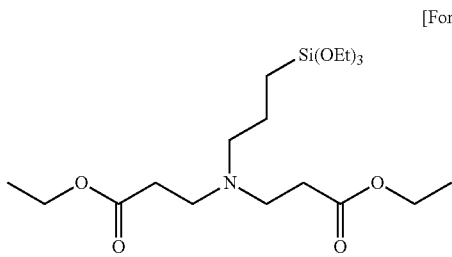

The terminal modified and conjugated diene-based polymer may have a number average molecular weight (Mn) of 1,000 to 2,000,000 g/mol, preferably, 10,000 to 2,000,000 g/mol, and more preferably, 100,000 to 2,000,000 g/mol.

The terminal modified and conjugated diene-based polymer may have a molecular weight distribution (Mw/Mn) of 1.05 to 10, preferably, 1.1 to 5, and more preferably, 1.1 to 4. When the molecular weight distribution of the terminal modified and conjugated diene-based polymer satisfies the above range, a rubber composition may have improved mechanical properties, low fuel consumption, and abrasion resistance.

The terminal modified and conjugated diene-based polymer may have a vinyl content of 5 wt % or more, preferably, 10 wt % or more, and more preferably, 15 to 70 wt %.

The vinyl content means an amount of a unit having a vinyl group, or an amount of a conjugated diene-based monomer which is not 1,4-added but 1,2-added, based on 100 wt % of a conjugated diene-based monomer.

If the vinyl content of the terminal modified and conjugated diene-based polymer satisfies such range, the glass transition temperature of a polymer may increase, satisfies physical properties required for a tire such as running resistance and breaking power when applied to the tire, and has decreasing effect of fuel consumption.

The terminal modified and conjugated diene-based polymer may include a conjugated diene-based polymer chain which is a polymer chain composed by including an aromatic vinyl-based monomer in an amount of 1 to 60 wt %, 10 to 50 wt %, or 15 to 40 wt % based on 100 wt % of the total amount of the conjugated diene-based monomer and vinyl-based aromatic monomer.

The polymer chain may be, for example, a random polymer chain.

According to an embodiment of the present invention, the method for preparing a terminal modified and conjugated diene-based polymer may further include adding a polar additive during polymerizing in step a). The polar additive is added because the polar additive controls the reaction rate of the conjugated diene-based monomer and the vinyl aromatic monomer.

The polar additive may be a base, or ether, amine, or a mixture thereof, and may particularly be, at least one selected from the group consisting of tetrahydrofuran, ditetrahydrofurylpropane, diethyl ether, cycloamyl ether, dipropyl ether, ethylene dimethyl ether, ethylene dimethyl ether, diethylene glycol, dimethyl ether, tertiary butoxyethoxyethane, bis(2-dimethylaminoethyl)ether, (dimethylaminoethyl) ethyl ether, trimethylamine, triethylamine, tripropylamine, and tetramethylethylenediamine, and may preferably be ditetrahydropropylpropane, triethylamine, or tetramethylethylenediamine.

The polar additive may be used in an amount of 0.001 to 50 g, 0.001 to 10 g, 0.005 to 1 g, or 0.005 to 0.1 g based on 100 g of the total amount of monomers injected.

In addition, the polar additive may be used in an amount of 0.001 to 10 g, 0.005 to 1 g, or 0.005 to 0.1 g, based on 1 mmol of the total molar amount of an organometallic compound injected.

When the conjugated diene-based monomer and the aromatic vinyl-based monomer are copolymerized, a block polymer may be mainly prepared due to the difference of reaction rates between them, but when the polar additive is added, the reaction rate of the vinyl aromatic monomer which has a slow reaction rate may increase, thereby attaining inducing effect of microstructure of a corresponding polymer, for example, a random polymer.

The polymerization in step a) may be, for example, an anionic polymerization, and particularly, the polymerization in step a) may be a living anionic polymerization in which an active terminal may be obtained through a propagation reaction by anions.

In addition, the polymerization in step a) may be, for example, polymerization with heating or polymerization at a constant temperature.

The polymerization with heating means a polymerization method including a step of elevating a reaction temperature by optionally applying heat after adding an organometallic compound, and the polymerization at a constant temperature means a polymerization method in which heat is not optionally applied after adding an organometallic compound.

The polymerization temperature of step a) may be, for example, from −20 to 200° C., from 0 to 150° C., or from 10 to 120° C.

Step b) may be, for example, a step of injecting at least one kind, or two or three kinds of the compound represented by Formula 1 or Formula 2.

In addition, step b) may be a step of conducting a reaction, for example, at 0 to 90° C. for 1 minute to 5 hours.

According to an embodiment of the present invention, step b) may be conducted by, for example, a batch type, or a continuous polymerization method including at least one reactor.

According to another aspect of the present invention, a tire or a tire tread, including the terminal modified and conjugated diene-based polymer rubber composition are provided.

MODE FOR CARRYING OUT THE INVENTION

Hereinafter, the present invention will be explained in particular referring to embodiments to assist the understanding of the present invention. However, the following embodiments may include various modifications, and the scope of the present invention should not be interpreted to be limited by the following embodiments. The embodiments of the present invention are provided to completely explain the present invention to a person having an ordinary knowledge in the art.

Example 1

To a 20 L, autoclave reactor, 270 g of styrene, 710 g of 1,3-butadiene, 5 kg of n-hexane, and 1.13 g of 2,2-di(2-tetrahydrofuryl)propane (DTP) as a polar additive were added, and the inner temperature of the reactor was elevated to 40° C. When the internal temperature of the reactor reached 40° C., 27.40 g (2.62 wt % in hexane, 33% activation) of n-butyllithium was added to the reactor, and an adiabatic heating reaction was conducted. After about 20 minutes, 20.0 g of 1,3-butadiene was added for capping the terminal of SSBR with butadiene. After 5 minutes, 1.65 g of dimethyl 2-((bis(3-(diethoxy(methyl)silyl)propyl)amino) methyl)succinate was added as a modifier and reacted for 15 minutes ([DPT]/[act. Li]=1.55, [modifier]/[act. Li]=0.82). Then, a polymerization reaction was terminated using ethanol, and 33 g of a hexane solution in which 30 wt % of Wingstay K was dissolved as an antioxidant was added thereto. The polymer thus obtained was put into water heated using steam, stirred to remove solvents, and roll dried to remove remaining solvent and water to prepare a terminal modified and conjugated diene-based polymer. Then, a sample was dried and GPC was measured.

Example 2

To a 20 L, autoclave reactor, 270 g of styrene, 710 g of 1,3-butadiene, 5 kg of n-hexane, and 0.92 g of 2,2-di(2-tetrahydrofuryl)propane (DTP) as a polar additive were added, and the inner temperature of the reactor was elevated to 40° C. When the internal temperature of the reactor reached 40° C., 22.40 g (2.62 wt % in hexane, 33% activation) of n-butyllithium was added to the reactor, and an adiabatic heating reaction was conducted. After about 20 minutes, 20.0 g of 1,3-butadiene was added for capping the terminal of SSBR with butadiene. After 5 minutes, 1.47 g of diethyl 3,3'-((3-(triethoxysilyl)propyl)azanediyl)dipropionate was added as a modifier and reacted for 15 minutes ([DPT]/[act. Li]=1.56, [modifier]/[act. Li]=0.92). Then, a polymerization reaction was terminated using ethanol, and 33.3 g of a hexane solution in which 30 wt % of Wingstay K was dissolved as an antioxidant was added thereto. The polymer thus obtained was put into water heated using steam, stirred to remove solvents, and roll dried to remove remaining solvent and water to prepare a terminal modified and conjugated diene-based polymer. Then, a sample was dried and GPC was measured.

Analysis results on the terminal modified and conjugated diene-based polymers thus prepared are shown in Table 1 below.

Comparative Example 1

A modified and conjugated diene-based polymer was prepared by the same method described in Example 1 except for injecting 1.2 mmol of dimethylchlorosilane as coupling agent. Analysis results on the modified and conjugated diene-based polymers thus prepared are shown in Table 1 below.

Comparative Example 2

A modified and conjugated diene-based polymer was prepared by the same method described in Example 1 except for injecting 1.1 mmol of ethyl 3-(cyclohexyl((triethoxysilyl)methyl)amino)propanoate which was made by the present inventors. Analysis results on the modified and conjugated diene-based polymers thus prepared are shown in Table 1 below.

The analysis of the conjugated diene-based polymers prepared in Examples 1 and 2 and Comparative Examples 1 and 2 were conducted via measurement according to the following methods.

1) Mooney viscosity: measured using MV-2000 manufactured by ALPHA Technologies Co., Ltd for two specimens having a weight of at least 15 g which were pre-heated for 1 minute and then heated at 100° C. for 4 minutes.

2) Styrene monomer (SM) content and vinyl content were measured by using NMR.

3) Weight average molecular weight (Mw), number average molecular weight (Mn) and molecular weight distribution (PDI): measured by GPC analysis under conditions of 40° C. Two columns of PLgel Olexis and one column of PLgel mixed-C manufactured by Polymer Laboratories Co. Ltd. were used in combination as columns, and newly replaced columns were all mixed bed type columns. In addition, polystyrene (PS) was used as a GPC standard material for calculating the molecular weight.

TABLE 1

| Division | | Example 1 | Example 2 | Comparative Example 1 | Comparative Example 2 |
| --- | --- | --- | --- | --- | --- |
| Polar additive (g) | | 1.2 | 1.1 | 0.9 | 1.1 |
| Modifier (mmol) | A | 2.3 | — | — | — |
| | B | — | 3.1 | — | — |
| | C | — | — | 1.2 | — |
| | D | — | — | — | 3.1 |
| Mooney viscosity (MV) | | 69 | 66 | 64 | 72 |
| NMR (%) | SM | 27.0 | 27.1 | 27.4 | 26.8 |
| | Vinyl | 43.5 | 43.6 | 43.1 | 44.1 |
| GPC ($\times 10^4$) | Mn | 29 | 23 | 31 | 38 |
| | PDI | 1.4 | 1.5 | 1.2 | 1.4 |

A: dimethyl 2-((bis(3-(diethoxy(methyl)silyl)propyl)amino)methyl)succinate
B: diethyl 3,3'-((3-(triethoxysilyl)propyl)azanediyl)dipropionate
C: dimethylchlorosilane
D: ethyl 3-(cyclohexyl((triethoxysilyl)methyl)amino)propanoate A conjugated diene-based polymer rubber composition was prepared by mixing each specimen among A, B, C and P shown in Table 1 as a raw material of rubber in mixing conditions shown in Table 2 below. The unit of the raw material in Table 2 is phr based on 100 parts by weight of rubber.

Particularly, each conjugated diene-based polymer rubber composition was mulled via a first stage mulling and a second stage mulling. In the first stage mulling, a raw material of rubber (conjugated diene-based polymer), a filler, an organosilane coupling agent, an oil, zinc oxide, a stearic acid antioxidant, an antiaging agent, wax and a promoter were mulled by using a banbury mixer equipped with a temperature controlling apparatus. In this case, the temperature of the mulling apparatus was controlled, and a first mixture was obtained at a discharge temperature of 145 to 155° C. In the second stage mulling, the first mixture was cooled to room temperature, and rubber, sulfur and a vulcanization accelerator were added to the mulling apparatus and mixed at a temperature of 100° C. or less to obtain a second mixture. Finally, a curing process was conducted at 160° C. for 20 minutes to prepare conjugated diene-based polymer rubber compositions of Preparation Examples 1 and 2 using the polymers of Examples 1 and 2 as rubber raw materials, and conjugated diene-based polymer rubber compositions of Comparative Preparation Examples 1 and 2 using the polymers of Comparative Examples 1 and 2 as rubber raw materials.

TABLE 2

| Division | Material | Amount (unit: phr) |
| --- | --- | --- |
| First stage mulling | Rubber | 137.5 |
| | Silica | 70.0 |
| | Coupling agent | 11.2 |
| | Oil (TDAE) | 25 |
| | Zinc oxide | 3.0 |

TABLE 2-continued

| Division | Material | Amount (unit: phr) |
| --- | --- | --- |
| | Stearic acid | 2.0 |
| | Antioxidant | 2.0 |
| | Antiaging agent | 2.0 |
| | Wax | 1.0 |
| Second stage mulling | Rubber accelerator | 1.75 |
| | Sulfur | 1.5 |
| | Vulcanization accelerator | 2.0 |
| | Total amount | 234.0 |

The physical properties of each rubber composition thus prepared were measured by the following methods.

1) Tensile Experiment

Tensile strength when breaking and tensile stress when elongating by 300% (300% modulus) of a specimen were measured according to an ASTM 412 tensile test method. A Universal Test machine 4204 tensile tester of Instron Co., Ltd. was used, and measurement was performed at room temperature at a tensile rate of 50 cm/min, to obtain measurement values of tensile strength, Modulus and elongation rate.

2) Viscoelasticity Properties

A dynamic mechanical analyzer of TA Co., Ltd was used. A Tan δ value was measured by changing deformation with a twist mode and a frequency of 10 Hz at each measurement temperature (−60 to 60° C.). Payne effect was represented by the difference between a minimum value and a maximum value at deformation of 0.28% to 40%. The smaller the payne effect was, the better the dispersibility of a filler such as silica was. If the Tan δ value at a low temperature of 0° C. was high, wet traction was good, and if the Tan δ value at a high temperature of 60° C. was low, hysteresis loss was small, low rolling resistance of a tire, i.e., low fuel consumption ratio was good. In Table 3, the physical properties of vulcanized rubber are shown.

TABLE 3

| Division | Preparation Example 1 | Preparation Example 2 | Comparative Preparation Example 1 | Comparative Preparation Example 2 |
| --- | --- | --- | --- | --- |
| 300% modulus (kgf/cm$^2$) | 132 | 148 | 104 | 132 |
| Tensile strength (kgf/cm$^2$) | 189 | 180 | 168 | 175 |
| Tan δ at 0° C. | 0.845 | 1.030 | 0.542 | 0.925 |
| Tan δ at 60° C. | 0.091 | 0.099 | 0.115 | 0.101 |

As shown in the results of Table 3, the terminal modified and conjugated diene-based polymer rubber compositions of Preparation Examples 1 and 2 according to the present invention had greatly increased 300% modulus (tensile stress) and tensile strength when compared to Comparative Preparation Example 1, and a significantly low Tan δ value at 60° C. Thus, when the terminal modified and conjugated diene-based polymer rubber composition of the present invention is included in a tire, rolling resistance may be lower than the conventional technique, and good fuel consumption ratio may be secured.

In addition, a carbonyl functional group included in the terminal modified and conjugated diene-based polymer compositions of Preparation Examples 1 and 2 according to the present invention has high reactivity with the terminal anion of rubber. Accordingly, when one ester group which has high reactivity with the terminal anion of rubber is increased, reactivity with the terminal anion may increase, and effect of producing highly modified polymer may be expected. The terminal modified and conjugated diene-based polymer rubber compositions of Preparation Examples 1 and 2 according to the present invention exhibited a higher Tan δ value at 0° C. than that of Comparative Preparation Example 1, and when a tire included the terminal modified and conjugated diene-based polymer rubber composition of the present invention, wet traction was confirmed high. In addition, since an alkoxysilane, an amine and a highly reactive carbonyl group with an anionic terminal were present in the modifier structure which was used in Preparation Examples 1 and 2 according to the present invention, all physical properties were increased when compared to those of Comparative Preparation Example 1.

In addition, the terminal modified and conjugated diene-based polymer rubber compositions including two carbonyl functional groups according to Preparation Examples 1 and 2, 300% modulus (tensile stress) and tensile strength were rapidly improved when compared to those of Comparative Preparation Example 2 in which one carbonyl function group was included. In addition, a Tan δ value at 0° C. for Preparation Example 2 was higher than that of Comparative Preparation Example 2, and when the terminal modified and conjugated diene-based polymer rubber composition was included in a tire, wet traction was even further improved. A Tan δ value at 60° C. in Preparation Example 1 or 2 was smaller than that of Comparative Example 2, and a lower rolling resistance value than a modifier including one carbonyl function group was attained, and fuel consumption ratio was secured to be good.

The invention claimed is:

1. A terminal modified and conjugated diene-based polymer rubber composition, comprising 100 parts by weight of a terminal modified and conjugated diene-based polymer in which an aminosilane-based terminal modifier represented by the following Formula 1 or Formula 2 is combined at a terminal of a conjugated diene-based polymer; and 0.1 to 200 parts by weight of an inorganic filler:

[Formula 1]

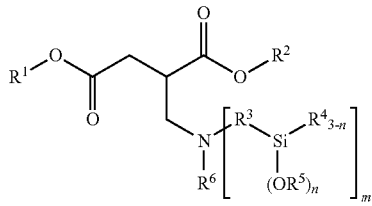

in Formula 1, $R^1$ and $R^2$ are $C_{1-20}$ hydrocarbon or $C_{1-20}$ hydrocarbon containing a heteroatom, $R^3$ is $C_{1-10}$ hydrocarbon, $R^4$ and $R^5$ are $C_{1-20}$ hydrocarbon, $R^6$ is $C_{1-10}$ hydrocarbon when m is 1, $R^6$ is absent when m is 2, n is an integer of 1-3, and m is an integer of 1-2;

[Formula 2]

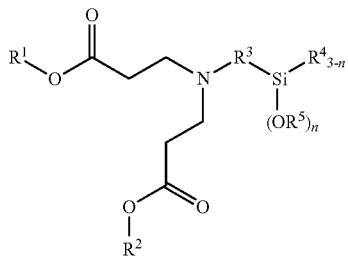

in Formula 2, $R^1$ and $R^2$ are $C_{1-20}$ hydrocarbon or $C_{1-20}$ hydrocarbon containing a heteroatom, $R^3$ is $C_{1-10}$ hydrocarbon, $R^4$ and $R^5$ are $C_{1-20}$ hydrocarbon, and n is an integer of 1-3.

2. The terminal modified and conjugated diene-based polymer rubber composition of claim 1, wherein the inorganic filler is at least one selected from the group consisting of a silica-based filler, carbon black, and a mixture thereof.

3. A method for preparing a terminal modified and conjugated diene-based polymer rubber composition, the method comprising:
a) polymerizing a conjugated diene-based monomer, or a conjugated diene-based monomer and an aromatic vinyl-based monomer in a solvent in the presence of an organometallic compound to form an active polymer having an alkali metal terminal;
b) injecting a compound represented by the following Formula 1 or Formula 2 to the active polymer having an alkali metal terminal and modifying to form a terminal modified and conjugated diene-based polymer; and
c) preparing a terminal modified and conjugated diene-based polymer rubber composition containing the terminal modified and conjugated diene-based polymer:

[Formula 1]

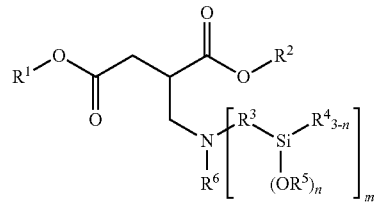

in Formula 1, $R^1$ and $R^2$ are $C_{1-20}$ hydrocarbon or $C_{1-20}$ hydrocarbon containing a heteroatom, $R^3$ is $C_{1-10}$ hydrocarbon, $R^4$ and $R^5$ are $C_{1-20}$ hydrocarbon, $R^6$ is $C_{1-10}$ hydrocarbon when m is 1, $R^6$ is absent when m is 2, n is an integer of 1-3, and m is an integer of 1-2;

[Formula 2]

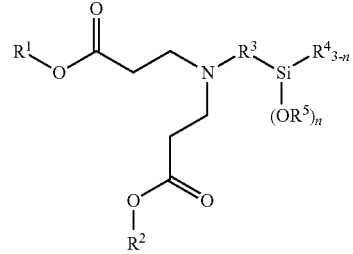

in Formula 2, $R^1$ and $R^2$ are $C_{1-20}$ hydrocarbon or $C_{1-20}$ hydrocarbon containing a heteroatom, $R^3$ is $C_{1-10}$ hydrocarbon, $R^4$ and $R^5$ are $C_{1-20}$ hydrocarbon, and n is an integer of 1-3.

4. The method for preparing a terminal modified and conjugated diene-based polymer rubber composition of claim 3, wherein
in Formula 1, $R^1$ and $R^2$ are $C_{1-10}$ alkyl or $C_{1-10}$ alkyl containing N, S or O; $R^3$ is $C_{1-10}$ alkylene;
$R^4$ and $R^5$ are $C_{1-20}$ alkyl; and $R^6$ is $C_{1-10}$ alkyl when m is 1, and in Formula 2, $R^1$ and $R^2$ are $C_{1-10}$ alkyl or $C_{1-10}$ alkyl containing N, S or O; $R^3$ is $C_{1-10}$ alkylene; and $R^4$ and $R^5$ are $C_{1-20}$ alkyl.

5. The method for preparing a terminal modified and conjugated diene-based polymer rubber composition of claim 3, wherein Formula 1 is represented by the following Formula 1a:

[Formula 1a]

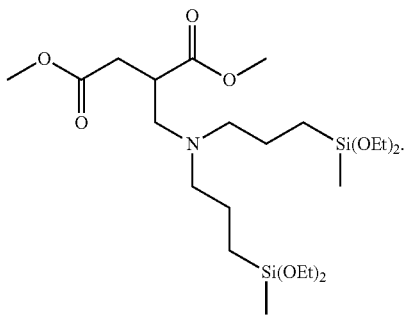

6. The method for preparing a terminal modified and conjugated diene-based polymer rubber composition of claim 3, wherein Formula 2 is represented by the following Formula 2a:

[Formula 2a]

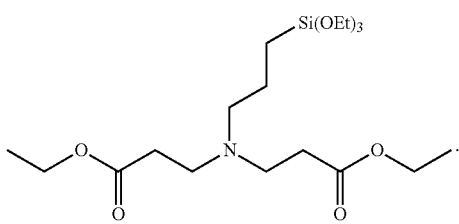

7. The method for preparing a terminal modified and conjugated diene-based polymer rubber composition of claim 3, wherein a molar ratio of the organometallic compound and the compound represented by Formula 1 or Formula 2 is from 1:0.1 to 1:10.

8. The method for preparing a terminal modified and conjugated diene-based polymer rubber composition of claim 3, further comprising injecting a polar additive in step a).

9. The method for preparing a terminal modified and conjugated diene-based polymer rubber composition of claim 8, wherein the polar additive is injected in an amount of 0.001 to 10 g based on the total of 1 mmol of the organometallic compound.

10. The method for preparing a terminal modified and conjugated diene-based polymer rubber composition of claim 3, wherein the terminal modified and conjugated diene-based polymer has a number average molecular weight (Mn) of 1,000 to 2,000,000 g/mol.

11. A tire or a tire tread, comprising the terminal modified and conjugated diene-based polymer rubber composition according to claim 1.

* * * * *